United States Patent [19]

Freedman

[11] Patent Number: 4,478,938

[45] Date of Patent: Oct. 23, 1984

[54] PROCESS FOR CROSSLINKING POLYAMINES

[75] Inventor: Harold H. Freedman, Newton Center, Mass.

[73] Assignee: The Dow Chemical Company, Midland, Mich.

[21] Appl. No.: 585,744

[22] Filed: Mar. 2, 1984

[51] Int. Cl.$^3$ .................. C12N 11/06; C07G 7/00; C08G 18/00; C08G 18/28
[52] U.S. Cl. .................. 435/181; 260/112 R; 260/112 B; 525/54.1; 527/204; 528/44; 528/68; 528/424
[58] Field of Search ............ 528/424, 68, 44; 525/54.1; 527/204; 435/181; 260/112 R, 112 B

[56] References Cited

U.S. PATENT DOCUMENTS

| | | | |
|---|---|---|---|
| 3,607,365 | 9/1971 | Lindlof | 528/68 X |
| 3,682,867 | 8/1972 | Schackelford et al. | 528/68 X |
| 3,788,948 | 1/1974 | Kagedal et al. | 260/112 R X |
| 3,789,027 | 1/1974 | Traubel et al. | 528/68 X |
| 4,087,413 | 5/1978 | Kelyman | 525/424 X |
| 4,177,038 | 12/1979 | Biebricher et al. | 435/181 X |
| 4,416,992 | 11/1983 | Arena et al. | 435/181 X |

*Primary Examiner*—Howard E. Schain

[57] ABSTRACT

Polyalkylenepolyamines are crosslinked in a non-anhydrous environment to yield water-swellable, essentially water-insoluble gels. The polyalkylenepolyamine is contacted with a polyisocyanate at a pH between about 5 and about 8 and subjected to a high rate of agitation. The process of this invention can be employed to immobilize proteins, enzymes, antibodies, etc.

12 Claims, No Drawings

PROCESS FOR CROSSLINKING POLYAMINES

BACKGROUND OF THE INVENTION

This invention relates to crosslinked polymers, and in particular, to crosslinked polymers which form water-swellable, water-insoluble gels.

Linear polyalkylenepolyamines are rendered water-insoluble through the addition of diisocyanates at a temperature between about 30° C. and about 200° C., using techniques disclosed in U.S. Pat. No. 4,087,413. Unfortunately, the resulting water-insoluble products are prepared either in neat form or in the presence of a suitable solvent. Reactions of amines with diisocyanates are disclosed in U.S. Pat. No. 4,177,038. However, it is typically necessary to prepare such products under essentially anhydrous conditions because isocyanates moieties are hydrolyzed rapidly by water to yield substituted ureas.

In view of the fact that polymers such as acylated polyalkylenepolyamines are water-soluble, and in view of the fact that it would be highly desirable to render such polymers water-insoluble in an aqueous medium; it would be highly desirable to provide a process for preparing a crosslinked polyalkenepolyamine in a non-anhydrous environment.

SUMMARY OF THE INVENTION

The present invention is a process for crosslinking a polyalkylenepolyamine wherein a polyisocyanate is contacted with an aqueous liquid comprising a polyalkylenepolyamine which is at a specific pH and which is subjected to a sufficiently high rate of shear agitation to yield a water-swellable, essentially water-insoluble gel. By the term "specific pH" is meant a pH which can range from slightly acidic to slightly basic.

The advantage of the process of this invention is that gelled materials can be prepared quickly and efficiently under conditions which do not require an anhydrous environment. The gels are useful in a wide variety of applications in which water-insoluble, swellable gels are useful. Of particular interest, are those uses in which a gel is useful as a biosupport for the isolation and purification of enzymes and other proteins.

Thus, in another aspect the present invention is a process for covalently immobilizing a protein wherein said protein is contacted with a polyalkylenepolyamine and a polyisocyanate in an aqueous liquid which is at a specific pH and which is subjected to a sufficiently high rate of agitation to yield a water-swellable, essentially water-insoluble gel.

The immobilized proteins are useful for a variety of uses. For example, immobilized proteins can be used as catalysts or in the purification of bioproducts.

DETAIL DESCRIPTION OF THE INVENTION

Polyalkylenepolyamines have repeating units which can be independently represented as follows:

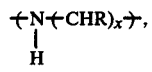  (I)

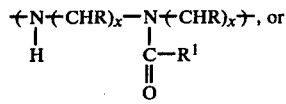  (II)

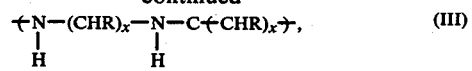  (III)

wherein R is independently hydrogen or a lower alkyl (e.g., about $C_1$ to about $C_3$ alkyl); $R^1$ is alkyl (e.g., about $C_1$ to about $C_{18}$ alkyl), aryl, alkyaryl or substituted alkyl, alkyaryl or aryl; and x is 2 or 3. Such types of polymers are prepared using techniques disclosed in U.S. Pat. No. 4,087,413, which is incorporated herein by reference. In general, the polyalkylenepolyamines of this invention are any water-soluble polyalkylenepolyamines containing secondary amine groups. The preferred polyalkylenepolyamine is polyethylenepolyimine. In the case of the partially hydrolyzed acylated polyamines, the extent of hydrolysis can range from about 10 to about 85, preferably about 50 weight percent, based on the weight of the polymerized monomers. Preferably, the molecular weight of the polyalkylenepolyamine can range from about 10,000 to about 1,000,000; most preferably from about 50,000 to about 75,000. Poor gels are obtained or no gelation occurs if the molecular weight of the polymer is not sufficiently high.

Organic polyisocyanates which can be employed include aromatic, aliphatic and cycloaliphatic polyisocyanates and combinations thereof. Representative of these types are the diisocyanates such as m-phenylene diisocyanate, tolylene-2,4-diisocyanate, tolulene-2,6-diisocyanate, hexamethylene-1,6-diisocyanate, tetramethylene-1,4-diisocyanate, cyclohexane-1,4-diisocyanate, hexahydrotolylene diisocyanate (and isomers), naphthylene-1,5-diisocyanate, 1-methoxyphenyl-2,4-diisocyanate, diphenylmethane-4,4-diisocyanate, 4,4'-biphenylene diisocyanate, 3,3'-dimethoxy-4,4'-biphenyl diisocyanate, 3,3'-dimethyl-4,4'-biphenyl diisocyanate, and 3,3'-dimethyldiphenylmethane-4,4'-diisocyanate; the triisocyanates such as 4,4',4'-triphenylmethane triisocyanate, polymethylene polyphenylisocyanate and tolylene-2,4,6-triisocyanate; and the tetraisocyanates such as 4,4'-dimethyldiphenylmethane-2,2',5,5'-tetraisocyanate. Especially useful due to their availability and properties are tolulene diisocyanate, diphenylmethane-4,4'-diisocyanate and polymethylene polyphenylisocyanate.

Crude polyisocyanate can also be used in the practice of the present invention, such as crude toluene diisocyanate obtained by the phosgenation of a mixture of toluene diamines or crude diphenylmethylene diisocyanate obtained by the phosgenation of crude diphenylmethylenediamine. The preferred undistilled or crude isocyanates are disclosed in U.S. Pat. No. 3,215,652.

The amount of polyisocyanate which is employed relative to the polyalkylenepolyamine can vary depending upon factors such as the reactivity of the species, the concentration of reactants relative to the aqueous liquid, the amount of crosslinking desired and the like. Preferably, the amount of polyisocyanate ranges from about 5 to about 25, preferably about 10 to about 15 weight percent, based on the weight of the dry polyalkylenepolyamine. Typically, poor gels are obtained or no gelation occurs if there is employed an insufficient amount of polyisocyanate.

The process of this invention is performed in an aqueous liquid. Preferably, the aqueous liquid comprises essentially water. As used herein, the term "aqueous liquid" means a liquid comprising water which can contain additives soluble therein or immiscible therewith. For example, the aqueous liquid can contain an aqueous phase comprising water and additives soluble therein, and a water immiscible organic solvent. The amount of the water immiscible organic solvent can range, for example, from about 0.5:1 to about 5:1 relative to the volume of the aqueous phase. Examples of water immiscible organic solvents include benzene, toluene, methylenechloride, chloroform, and the like.

Typically, depending upon the polyamine, the pH of the aqueous liquid can range from about 4 to about 9, preferably 5 to about 8, more preferably from about 5 to about 7.5, most preferably from about 6 to about 6.5. The pH of the aqueous liquid is critical as the rate of crosslinking is sensitive to pH. That is, for example, the crosslinking reaction can occur too quickly if the pH is exceedingly low. Conversely, the crosslinking reaction can occur very slowly if the pH is exceedingly high. In addition, poor gels obtained or no gelation occurs if the pH of the aqueous liquid is not within a suitable (i.e., specific) range. The pH typically decreases by a small amount (i.e., less than about 1 unit) during the crosslinking reaction. This change in pH can be controlled by a suitable buffer.

The amount of aqueous liquid which is employed depends upon the molecular weight and the amount of polyalkylenepolyamine which is employed. Typically, poor gelation occurs if the polymer solution is very dilute or the molecular weight of the polymer is very low. Conversely, the formation of desirable gels is a difficult process to perform if the polymer concentration in the aqueous liquid is very high or the molecular weight of the polymer is very high. Preferably, the amount of polyalkylenepolyamine present in the aqueous liquid can range from about 10 to about 50, preferably from about 20 to about 30 weight percent, based on the weight of the polymer and aqueous liquid.

The temperature at which the process of this invention is performed is not particularly critical and can vary. Typically, crosslinking can occur at room temperature. However, the aqueous liquid can also be heated above about 30° C.

The process of this invention is highly dependent upon the rate of agitation to which the aqueous polyalkyleneamine/polyisocyanate mixture is subjected. Little or no gellation occurs when a conventional magnetic stirrer or mechanical stirrer is employed as an agitation device. For this reason, it is necessary to provide a sufficiently high rate of agitation using a device such as a homogenizer, ultra-sonic stirring device or blender. Typically, the agitation rate should exceed about 3,000 rpm. Preferred agitation rates range from about 5,000 rpm to about 50,000 rpm, most preferably from about 10,000 rpm to about 20,000 rpm. It is understood that practically any device capable of providing such a high rate of agitation can be effectively employed.

The polyalkyleneamine/polyisocyanate mixture is subjected to a high rate of agitation for a period of time which can vary. For example, the period of time over which the mixture is subjected to agitation can depend upon factors such as the amount of reactants, the concentration of reactants in the aqueous liquid, etc. Typically, the period of time over which the mixture is subjected to agitation can range from about 2 seconds to several seconds, most preferably from about 3 seconds to about 5 seconds.

In the situation in which a two phase (i.e., aqueous solvent and water-immiscible solvent) solvent system is employed, hydrolysis of the isocyanate is believed to be retarded. Thus, conventional stirring devices such as magnetic stirrers or mechanical stirrers can be employed to yield good results. However, the rate of crosslinking is much slower than that observed when high rates of agitation are employed. That is, reaction times ranging from several minutes to about 1 hour may be necessary for sufficient crosslinking to occur. In any event, the actual reaction time can depend upon factors such as the particular polymer, the isocyanate concentration, the relative amount of solvent, the proportions of aqueous phase and water immiscible phase, etc.

After the mixture is subjected to agitation, the mixture is allowed to settle for a period of time sufficient for gellation to be completed. This period of time ranges from about 10 minutes to about 60 minutes, preferably from about 15 to about 20 minutes.

The process of this invention is most preferably carried out in a predominately aqueous phase. It is understood that most additives common in an aqueous liquid can be present. For convenience purposes, the water-soluble polyalkylenepolyamine is dispersed in the aqueous liquid and a solution is formed, which solution has the appropriate pH. This solution is contacted with the polyisocyanate, and the mixture is subjected to a sufficiently high rate of agitiation for a short period of time. The mixture is then allowed to gel. If desired, the resulting gel can be dispersed in an aqueous liquid by providing further agitation. In any case, the gel can be further treated, as desired, for the particular application for which it is employed.

Proteins containing free primary amine groups, such as enzymes and antibodies, can be immobilized using the process of this invention. For example, glucose oxidase, esterase, catalase, alkaline phosphatase, and the like can be easily and effectively immobilized. Preferably, the polyalkylenepolyamine, polyisocyanate and protein are contacted in the suitable solution at the suitable pH and subjected to the appropriate agitation. Typically, the amount of protein which is employed ranges from about 0.1 to about 10 milligrams per milliliter of polyalkylenepolyamine which is employed.

When employed as a biosupport for enzyme immobilization, the reaction conditions under which the gels are formed can be modified in accordance with the requirements necessary for the individual enzyme. Covalent attachment of the enzyme to the gel is believed to occur during the mixing and gellation stages. It is believed that immobilization occurs via the reaction of free isocyanate moieties of the gel with amino moieties of the protein. If desired, the enzyme active site can be protected from reaction by the presence of suitable enzyme substrates and/or products. The amount of immobilized protein can vary. The enzyme activity of the immobilized enzyme can also vary and is typically from 20 to about 80 percent of its original value.

The gels which are prepared are very hydrophilic, though essentially water-insoluble. When dry, the gels are amorphous, hard, solid materials which can be easily handled. When fully hydrated, the gels are transparent to translucent, soft, compressible solids which are insoluble in water.

The gels can be employed as water adsorbent materials, insoluble chelants for metals, insoluble modifiers of pH for aqueous systems, biosupports, and other such uses.

The following examples are presented to further illustrate but not limit the scope of this invention.

EXAMPLE 1

A 50 percent aqueous solution of polymer is prepared by dispersing 5 grams (g) of a high molecular weight polyethyleneimine in water. The pH of the solution is adjusted to 6.5 using concentrated hydrochloric acid. The solution is diluted with water to yield a solution containing 30 percent polyethyleneimine. To this solution is added 0.2 g hexamethylene-diisocyanate. The mixture is homogenized using a blender (agitation rate is about 10,000 rpm) for about 5 seconds. The mixture is allowed to stand for 20 minutes. The resulting firm gel is broken into pieces, stirred with 100 ml water and centrifuged for about 5 minutes. The supernatant liquid is decanted. The resulting gel has a volume of about 50 ml at a pH of about 5.

EXAMPLE 2

A 25 percent aqueous solution of polymer is prepared by dispersing 5 g of said polymer in water in an amount sufficient to provide a 20 ml aqueous solution. The polymer is a 50 percent hydrolyzed polyethyloxazoline having a molecular weight of about 50,000. The pH of the solution is adjusted to 8 using hydrochloric acid. The solution is magnetically stirred in a beaker and 15 ml of methylene chloride and 0.4 ml of 1,6-hexamethylene diisocyanate is added thereto. The mixture is rapidly stirred for about 15 minutes using a magnetic stirrer set at the highest obtainable speed (estimated at 200 rpm). The mixture is allowed to stand for 1 hour. The product is triturated 3 times with 40 ml each of acetone. The resulting white, acetone-swollen gel is dried to give about 4 g of white granular solid.

EXAMPLE 3

The immobilization of glucose oxidase (GOD) using polyethyleneimine is performed as follows.

To 1 ml of an aqueous polyethylimine solution (obtained from Aceto Chemicals, under the specification PEI-1,000) and adjusted to pH 6.1 and concentration of 0.25 g/ml is added 1 ml of aqueous solution containing about 50 units (U) GOD and 20 μl of 1,6,-hexamethylene dissocyanate and the mixture is homogenized for 5 seconds using a laboratory model Ross homogenizer at its maximum speed. The gel is allowed to sit for 15 minutes, diluted to 20 ml with water and dispersed by stirring at low speed in a 3-speed Waring Blender. The total gel, (20 ml) which assays for 35 U is centrifuged and the supernatant (6 ml) is decanted. The supernatant assays for 4 U and the washed gel containing the immobilized GOD assays for 33 U. After sitting at room temperature for 1 week, the gel assays for 38 U.

EXAMPLE 4

The immobilization of esterase using hydrolyzed polyethyloxazoline is performed as follows.

To 5 ml of a 15 percent solution of 50 percent hydrolyzed polyethyloxazoline (M.W.=50 M, pH 7.6) is added 100 μl of esterase (about 100 U) and 200 μl 1,6,-hexamethylene diisocyanate and the mixture is homogenized for about 10 seconds on a Vertis Model 45 homogenizer set at medium speed and left for 1 hour. The firm gel is chopped up in a Waring Blender with 10 ml of water, made up to 20 ml, stirred for 30 minutes and then centrifuged. The supernatant has no activity and the gel assays for 50 U. The yield of immobilized esterase is 50 percent.

What is claimed is:

1. A process for crosslinking a polyalkylenepolyamine wherein a polyisocyanate is contacted with an aqueous liquid comprising a polyalkylenepolyamine which is at a specific pH and which is subjected to a sufficiently high rate of agitation to yield a water-swellable, essentially water-insoluble gel.

2. A process of claim 1 wherein said aqueous liquid comprises essentially water.

3. A process of claim 2 wherein the rate of agitation is in excess of about 3,000 rpm.

4. A process of claim 1 wherein said specific pH ranges from about 5 to about 8.

5. A process of claim 1 wherein said aqueous liquid comprises water and a water immiscible organic solvent.

6. A process of claim 1 wherein said polyalkylenepolyamine has repeating units which are independently represented as:

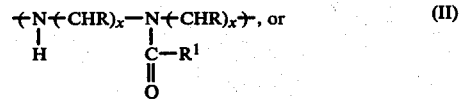

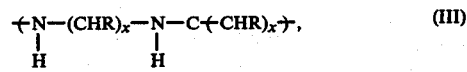

wherein R is independently hydrogen or a lower alkyl; $R^1$ is alkyl aryl or substituted alkyl or aryl; and x is 2 or 3.

7. A process of claim 1 wherein said polyalkylenepolyamine is polyethylenepolyimine.

8. A process of claim 1 wherein said polyisocyanate is a diisocyanate.

9. A process of claim 1 wherein said aqueous liquid comprises a protein.

10. A process of claim 9 wherein said protein is an enzyme.

11. A process for covalently immobilizing a protein wherein said protein is contacted with a polyalkylenepolyamine and a polyisocyanate in an aqueous liquid which is at a specific pH and which is subjected to a sufficiently high rate of agitation to yield a water-swellable, essentially water-insoluble gel.

12. A process of claim 11 wherein said protein is an enzyme.

* * * * *